US008314118B2

(12) United States Patent
Zagon et al.

(10) Patent No.: US 8,314,118 B2
(45) Date of Patent: Nov. 20, 2012

(54) METHODS AND COMPOSITIONS FOR TREATING DRY EYE

(76) Inventors: Ian S. Zagon, Hummelstown, PA (US); Patricia J. McLaughlin, Harrisburg, PA (US); Joseph W. Sassani, Hershey, PA (US)

(*) Notice: Subject to any disclaimer, the term of this patent is extended or adjusted under 35 U.S.C. 154(b) by 216 days.

(21) Appl. No.: 12/760,658

(22) Filed: Apr. 15, 2010

(65) Prior Publication Data
US 2010/0273821 A1 Oct. 28, 2010

Related U.S. Application Data

(60) Provisional application No. 61/173,351, filed on Apr. 28, 2009.

(51) Int. Cl.
*A61K 31/44* (2006.01)
(52) U.S. Cl. ..................... 514/282; 514/912
(58) Field of Classification Search ............ 514/282, 514/912
See application file for complete search history.

(56) References Cited

U.S. PATENT DOCUMENTS

| 7,189,697 | B2 | 3/2007 | Panjwani |
| 7,247,623 | B2 | 7/2007 | Yerxa et al. |
| 7,381,707 | B2 | 6/2008 | Lin et al. |
| 2006/0270592 | A1 | 11/2006 | Ousler, III et al. |

OTHER PUBLICATIONS

Smith, J.A. et al., "The Epidemiology of Dry Eye Disease: Report of the Epidemiology Subcommittee of the International Dry Eye Workshop" *The Ocular Surface* (2007) pp. 93-107, vol. 5(2).
Lemp, M.A. et al., "The Definition and Classification of Dry Eye Disease: Report of the Definition and Classification Subcommittee of the International Dry Eye Workshop" *The Ocular Surface* (2007) pp. 75-92, vol. 5(2).
Pflugfelder, S.C. et al., "Management and Thereapy of Dry Eye Disease: Report of the Management and Thereapy Subcommittee of the International Dry Eye Workshop" *The Ocular Surface* (2007) pp. 163-178, vol. 5(2).
Gipson, I.K. et al., "Research in Dry Eye: Report of the Research Subcommittee of the International Dry Eye Workshop" *The Ocular Surface* (2007) pp. 179-193, vol. 5(2).
Klocek, M.S. et al., "Topically Applied Naltrexone Restores Corneal Reepithelialization in Diabetic Rats" *Journal of Ocular Pharmacology and Therapeutics* (2007) pp. 89-102, vol. 23(2).
Zagon, I.S. et al., "Corneal Safety of Topically Applied Naltrexone" *Journal of Ocular Pharmacology and Therapeutics* (2006) pp. 377-387, vol. 22(5).
Zagon, I.S. et al., "Dry Eye Reversal and Corneal Sensation Restoration with Topical Naltrexone in Diabetes Mellitus" *Arch Ophthalmology* (2009) pp. 1468-1473, vol. 127(11).
Zagon, I.S. et al., "Naltrexone, an Opioid Antagonist, Facilitates Reepithelialization of the Cornea in Diabetic Rat" *Diabetes* (2002) pp. 3055-3062, vol. 51.
Zagon, I.S. et al., "Use of Topical Insulin to Normalize Corneal Epithelial Healing in Diabetes Mellitus" *Arch Ophthalmology* (2007) pp. 1082-1088, vol. 125(8).
Gilbard, J.P. et al. "Tear Film Osmolarity and Ocular Surface Disease in Two Rabbit Models for Keratoconjunctivits Sicca" *Investigative Ophthalmology & Visual Science* (1988) pp. 374-378, vol. 29(3).
Salvatore, M.F. et al., "Denervation of Rabbit Lacrimal Gland Increases Levels of Transferrin and Unidentified Tear Proteins of 44 and 36 kDa" *Current Eye Research* (1999) pp. 455-466, vol. 18(6).
Nagelhout, T.J. et al., "Preservation of Tear Film Integrity and Inhibition of Corneal Injury by Dexamethasone in a Rabbit Model of Lacrimal Gland Inflammation-Induced Dry Eye" *Journal of Ocular Pharmacology and Therapeutics* (2005) pp. 139-148, vol. 21(2).
Stewart, P. et al., "Effect of Experimental Dry Eye on Tear Sodium Concentration in the Mouse" *Eye & Contact Lens* (2005) pp. 175-178, vol. 31(4).
Zagon, I.S. et al., "Reepithelialization of the Human Cornea is Regulated by Endogenous Opioids" *Investigative Ophthalmology & Visual Science* (2000) pp. 73-81, vol. 41(1).
Song, X.J. et al., "Neuturin-Deficient Mice Develop Dry Eye and Keratoconjunctivitis Sicca" *Investigative Ophthalmology & Visual Science* (2003) pp. 4223-4229, vol. 44(10).
Sassani, J.W. et al., "Opioid Growth Factor Modulation of Corneal Epithelium: Uppers and Downers" *Current Eye Research* (2003) pp. 249-262, vol. 26(5).
Zagon, I.S. et al., "Naltrexone as a Novel Treatment for Diabetic Keratopathy: Toxicity Studies" *Oasis-Online Abstract Submission and Invitation Sysystem-Program Planner* Presentation Time: May 2, 2006 11:15am-1:00pm, Program # 2762, Poster # B157.
Klocek, M.S. et al., "Corneal Vascularization and Granulation Tissue Formation Accompanying Delayed Corneal Epithelial Wound Healing in Diabetic Rats is Prevented by Topical Treatment with Naltrexone" *Oasis-Online Abstract Submission and Invitation System-Program Planner* Presentation Time: May 7, 2007, 11:15am-1:00pm, Program # 1694, Poster # B554.
Sassani, J.W. et al., "Topical Treatment with Naltrexone and Insulin Does Not Have an Additive Effect on Accelerating Corneal Epithelial Healing in Type I Diabetic Rats" *Oasis-Online Abstract Submission and Invitation System-Program Planner* Presentation Time: Apr. 29, 2008, 3:00pm-4:45pm, Program # 3398, Poster # A252.
Sassani, J.W. et al., "Corneal Epithelial Adhesion Complexes are not Altered in Diabetic Rats Following Topical Naltrexone Therapy" *Oasis-Online Abstract Submission and Invitation System-Program Planner* Presentation Time: May 8, 2007, 3:00pm-4:45pm, Program # 3481, Poster # B872.
Klocek, M.S. et al., "Naltrexone as a Novel Treatment of Diabetic Keratopathy: Efficacy Studies" *Oasis-Online Abstract Submission and Invitation System-Program Planner* Presentation Time: May 2, 2006, 11:15am-1:00pm, Program # 2761, Poster # B156. Zagon, I. et al., "Prevention of Exuberant Granulation Tissue and Neovascularization in the Rat Cornea by Naltrexone" *Arch Opthalmol.* (2008) pp. 501-506 vol. 126(4).
International Search Report dated Jan. 18, 2011.

*Primary Examiner* — Zohreh Fay
(74) *Attorney, Agent, or Firm* — Scully, Scott, Murphy & Presser, P.C.

(57) ABSTRACT

This invention relates to treatment of dry eye. In particular, the invention relates to methods and formulations for treating dry eye based on topical application of opioid antagonists such as naltrexone.

8 Claims, 7 Drawing Sheets

NTX 1 Drop

NTX 1 Day Q.I.D.

NTX 5 Days Q.I.D.

Insulin 1 Drop

Schirmer's Test

Corneal Sensitivity

METHODS AND COMPOSITIONS FOR TREATING DRY EYE

CROSS REFERENCE TO RELATED APPLICATION

This application claims the benefit of priority from U.S. Provisional Application No. 61/173,351, filed on Apr. 28, 2009.

STATEMENT REGARDING GOVERNMENT SUPPORT

This invention was made with government support under grant EY16666 from the National Institutes of Health. The Government has certain rights in this invention.

FIELD OF THE INVENTION

This invention relates to treatment of dry eye. In particular, the invention relates to methods and formulations for treating dry eye based on topical application of opioid antagonists such as naltrexone.

BACKGROUND OF THE INVENTION

Dry eye is a disorder of the tear film due to tear deficiency or excessive tear evaporation which causes damage to the interpalpebral ocular surface associated with symptoms of ocular discomfort (Smith, *The Ocular Surface* 5(2): 93-407 (2007)). Chronic dryness leads to pain and irritation that is often debilitating to the subject, preventing the performance of normal daily activities such as reading, driving, among other things. Dry eye is increasing in prevalence as population ages. Approximately 4.9 million Americans 50 years and older have dry eye, and many more have less severe symptoms notable only during contact with adverse contributing factors such as low humidity or contact lens wear (Smith, 2007), as well as the 21 million individuals with diabetes. The number of women affected with dry eye appears to exceed that of men.

Currently dry eye includes two major classes: aqueous tear-deficient dry eye (ADDE) and evaporative dry eye (EDE). ADDE mainly refers to a failure of reflex lacrimal secretion, but also includes a failure of non-reflex water secretion by the conjunctiva. ADDE has two major subclasses, Sjogren Syndrome dry eye (SSDE) and non-SS dry eye. EDE may be intrinsic, where dry eye is due to intrinsic disease affecting lid structures or dynamics, or extrinsic, where ocular surface disease occurs due to some extrinsic exposure such as topical drug preservatives, contact lens wear or vitamin A deficiency. See review by Lemp, *The Ocular Surface* 5(2): 75-92 (2007).

Substantiated risk factors for developing dry eye include female sex, older age, postmenopausal estrogen therapy, diabetes mellitus, a diet that is low in omega 3 essential fatty acids or has a high ratio of omega 6 to omega 3 fatty acids, refractive surgery, vitamin A deficiency, radiation therapy, bone marrow transplant, hepatitis C, certain classes of systemic and ocular medications including anti-histamines (Smith, 2007). Other risk factors may include HIV, human T cell lymphotropic virus-1 infection, connective tissue diseases, systemic cancer chemotherapy, and certain other medications (Smith, 2007).

Current therapies for dry eye include tear supplementation (e.g., lubricants), tear retention, tear stimulation, tear substitutes, anti-inflammatory therapy, and essentially fatty acids, as discussed in a review article (Pflugfelder, *The Ocular Surface* 5(2): 163-178, 2007). Over-the-counter lubricants are most frequently prescribed by vision specialists; however lubricants offer only temporary relief, can be expensive, and need to be taken for life. The cause of dry eye is not treated with lubricants.

SUMMARY OF THE INVENTION

In one embodiment, the present invention is directed to a method of treating dry eye by administering topically an effective amount of an opioid antagonist to a subject in need thereof. In a specific embodiment, the opioid antagonist being administered is naltrexone. In another specific embodiment, the opioid antagonist being administered is naloxone.

In another embodiment, the present invention provides a composition for the treatment of dry eye, which contains an effective amount of an opioid antagonist and a pharmaceutically acceptable carrier suitable for topical administration. In a preferred embodiment, the opioid antagonist provided in the composition is naltrexone. In another specific embodiment, the opioid antagonist being administered is naloxone.

DETAILED DESCRIPTION OF THE INVENTION

Figure 1A:
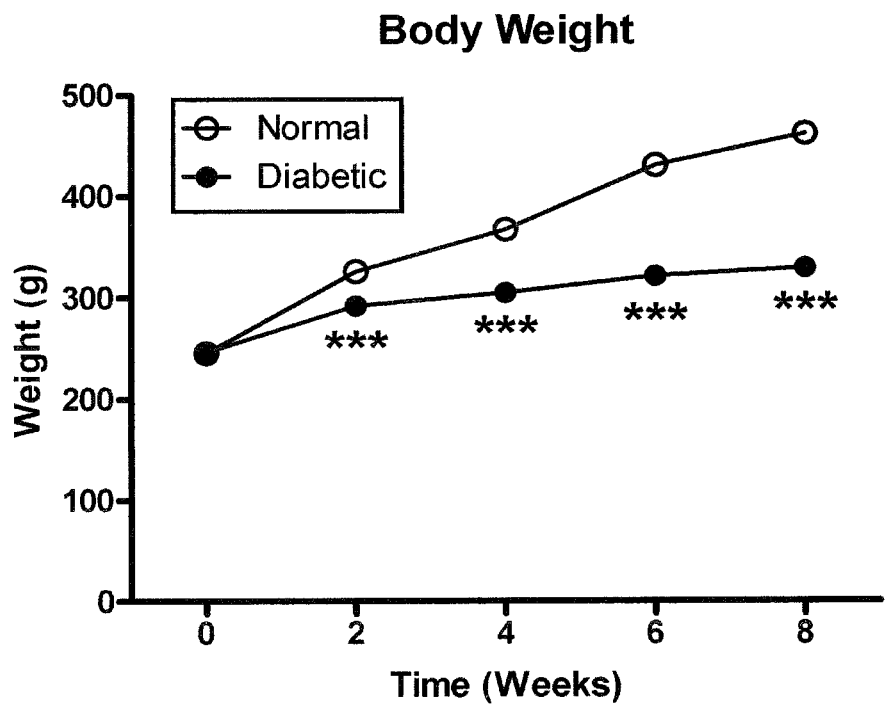
FIGS. 1A-1B. Body weights (1A) and glucose levels (1B) of rats rendered diabetic with STZ (Diabetic) or untreated animals receiving vehicle (Normal). (1A) Body weights were recorded at the time of STZ injection (week 0), and every 2 weeks thereafter. (1B) Blood glucose levels were recorded 1, 4, and 8 weeks after administration of STZ. Data are expressed as means±SEM for 15 Normal and 25 Diabetic animals at each time point. Significantly different from Normal rats at $p<0.001$ (***).

It has been surprisingly discovered that an opioid antagonist, such as naltrexone hydrochloride, when used at appropriate concentrations, rapidly reverses dry eye conditions with as little as only one daily topical application, and this effect can last for more than 2 days. Accordingly, the present invention provides therapeutic methods and compositions for treating dry eye based on use of naltrexone and other opioid antagonists.

Opioid antagonists, such as naltrexone and naloxone, are known as antagonists of an opioid receptor and are used primarily in the management of dependence on drugs (e.g., opioids), alcohol, and nicotine. The IUPAC name for naltrexone is 17-(cyclopropylmethyl)-4,5α-epoxy-3,14-dihydroxymorphinan-6-one. Naltrexone can be described as a substituted oxymorphone, where the tertiary amine methyl-substituent is replaced with methylcyclopropane. Naloxone is also known as dihydroxymorphinan-6-one. For purposes of the present invention, both naltrexone and naloxone, as well as pharmaceutically acceptable salts thereof (e.g., naltrexone hydrochloride, and naloxone hydrochloride) are suitable for use in the treatment of dry eye.

Without being bound to any particular theory, it is believed that elevated levels of opioids in dry eye patients depress neurotransmission in nerves regulating secretion of tears. Naltrexone interrupts the depressive effect exerted by opioid-opioid receptor interactions, thereby releasing glands to secrete tears. In addition, the excess of some opioids (Met-enkephalin) in at least some individuals suffering from dry eye act as growth factors (termed opioid growth factor) and depress cell proliferation of glandular cells. Naltrexone interrupts the interfacing of opioids from classical opioid receptors, thereby blocking the inhibitory action of this opioid system on neurotransmission, as well as blocking the opioid growth factor from its non-classical opioid receptor, opioid growth factor receptor, and stimulating cell proliferation of secretory cells.

In accordance with the present invention, the therapeutic method of treating dry eye involves identifying a subject suffering from dry eye symptoms, and administering to the eyes of such subject an effective amount of naltrexone or other opioid antagonists.

Subjects contemplated by the present invention include any mammalian subjects, particularly human subjects, dogs, cats and horses. Although dry eye may occur in diabetic patients, a large population of normal, non-diabetic individuals also suffer dry eye. The composition and method of the present invention can treat both diabetic and non-diabetic subjects.

Dry eye symptoms can include dryness, sandy feeling, burning, redness, crusting on lashes, itchiness not related to allergy, stickiness, and eyes stuck shut in the morning.

By "treating dry eye" it is meant to include complete or partial alleviation of all or some of symptoms of dry eye, and/or prevention or inhibition of the symptoms of dry eye. The treatment includes, but is not limited to, for example, promoting basal lacrimal secretion.

A composition containing an opioid antagonist such as naltrexone or naloxone can be administered topically to the eye or eyes of a subject suffering from dry eye. Topical administration includes directly applying, laying, or spreading on or around the eye, e.g., by use of an applicator such as a wipe, a contact lens, a dropper, or a spray.

A composition containing an opioid antagonist is formulated for convenient topical administration. Forms of the composition include, but are not limited to, solutions, ointments, gels, emulsions, suspensions, gel shields, and the like.

In one embodiment, naltrexone or another opioid antagonist is contained in an aqueous-based cream excipient, which can be applied to the eye at bedtime, but may also be applied any time throughout the day.

In another embodiment, a composition containing an opioid antagonist such as naltrexone or naloxone is formulated as a solution or suspension and is applied topically in the form of eye drops. Any solution suitable for topical application in which an opioid antagonist (such as naltrexone or naloxone) is soluble can be used; e.g., sterile water, Sorenson's phosphate buffer. In one embodiment, the composition can be incorporated in eye drop solutions for contact lens, washing solutions for contact lens, or preserving solutions for contact lens.

In other embodiments, a composition containing an opioid antagonist is made to have properties such as sustained-release or improved stability. For example, a polymeric matrix composition containing naltrexone can be topically applied to the eye to achieve sustained release.

Compositions containing an opioid antagonist can include additional ingredients, additives or carrier suitable for use in contact on or around the eye without undue toxicity, incompatibility, instability, irritation, allergic response, and the like. Additives such as solvents, bases, solution adjuvants, suspending agents, thickening agents, emulsifying agents, stabilizing agents, buffering agents, isotonicity adjusting agents, soothing agents, preservatives, corrigents, flavoring agents, coloring agents, excipients, binding agents, lubricants, surfactants, absorption-promoting agents, dispersing agents, preservatives, solubilizing agents, and the like, can be added to a formulation where appropriate.

The opioid antagonist-containing compositions of the present invention can include other active agents for treatment of dry eye, including, but not limiting to, anti-infective agents, antibiotics, antiviral agents, anti-inflammatory drugs, anti-allergic agents including anti-histamines, vasoconstrictors, vasodilators, local anesthetics, analgesics, intraocular pressure-lowering agents, immunoregulators, anti-oxidants, vitamins and minerals, proteases and peptidases that breakdown endogenous opioids, and the like.

An opioid antagonist-containing composition of the present invention is being administered to a subject in need thereof at an effective amount to treat the dry eye condition. The effective amount of the composition for a particular individual can depend on the severity of the condition of the individual, the type of formulation being applied, the frequency of administration, and the duration of the treatment. It has been found in accordance with the present invention that administration of an opioid antagonist such as, e.g., naltrexone, even at relatively low concentrations in liquid drops, e.g., at least $10^{-7}$ M, at least 0.5 to $1 \times 10^{-6}$ M, at least 0.5 to $1 \times 10^{-5}$ M, at least 0.5 to $1 \times 10^{-5}$ M, or at least 0.5 to $1 \times 10^{-3}$ M, or any concentration falling in a range between these values (e.g., $10^{-7}$ M to $10^{-3}$ M), reverses dry eye conditions with only one, or one to two, daily applications and does so rapidly. For example, naltrexone given at one to two drops ($10^{-6}$ M) reverses dry eye conditions rapidly within an hour or so, and the therapeutic effect lasts for 48 hours, while the therapeutic effect of naltrxone given at four drops ($10^{-6}$ M) over a twelve-hour period lasts at least 72 hours.

The present invention will be further illustrated by, but not limited to, the following examples.

Example 1

A Rat Model of Dry Eye

Methods
Animals and Induction of Diabetes

Male Sprague-Dawley rats (~245 g) were obtained from Charles River Laboratories (Wilmington, Mass.) and housed under standard laboratory conditions. All investigations conformed to the regulations of the ARVO, National Institutes of Health, and the guidelines of the Department of Comparative Medicine of The Pennsylvania State University.

Type 1 diabetes was induced according to previously reported procedures (Zagon et al., *Diabetes.* 2002; 51: 3055-3062; Klocek et al., *J Ocular Pharmacol Therapeutics.* 2007; 23:89-102; Zagon et al., *Arch Opthalmol.* 2007; 125:1082-1088). Briefly, an intraperitoneal (i.p.) injection of 40 mg/kg streptozotocin (STZ, Sigma, St. Louis, Mo.) in ice-cold 0.5 mol/l citrate buffer (pH 4.5) was administered. A second dose of STZ (40 mg/kg) was injected 24 hours later. This regimen produced insulin-deficient diabetes in 100% of the animals within 48 to 72 hours; these animals were termed DB rats (n=25). Fifteen animals not receiving STZ, but injected with citrate buffer, were considered Normal.

Blood glucose levels were monitored from the tail vein using a True Track Smart System glucometer (Home Diagnostics, Inc., Ft. Lauderdale, Fla.) immediately prior to receiving STZ and at 1, 4 and 8 weeks after injection of STZ. Glucose levels of >400 mg/dl were considered the minimum blood glucose level compatible with a stable non-toxic diabetic state.

Schirmer Test

Tear secretion was measured with Schirmer strips (Alcon Laboratories, Inc., Ft. Worth Tex.). A standard 17 mm long Schirmer strip was inserted into the lower cul-de-sac for 1 min. The strip wetting length was measured to the nearest millimeter. Five minutes prior to administration of the Schirmer strip, animals received topical Proparacaine Hydrochloride Ophthalmic Solution 0.5% (Akorn, Inc., Buffalo Grove, Ill.). Testing began 1 hour after the last drop of NTX or vehicle was administered, and continued every 24 hours thereafter.

Corneal Sensitivity

Corneal sensitivity was determined by an aesthesiometer (Cachet and Bonnet-Aesthesiometer, Boca Raton, Fla.). The values (g/mm$^2$) were determined directly from the protocol (and conversion table) supplied by the manufacturer.

Measurements of sensitivity were conducted prior to the Schirmer test.

Slit-Lamp Observations

To examine general overall morphology and pathology (e.g., corneal edema, scarring), observations with a hand-held slit lamp (Zeiss HSO 10 Hand Slit Lamp, Dublin, Calif.) were conducted.

Topical Administration of Naltrexone

Naltrexone hydrochloride (Sigma-Aldrich, Indianapolis, Ind.) was prepared in Vigamox (moxifloxacin hydrochloride ophthalmic solution, Alcon, Inc, Ft. Worth, Tex.) at a $10^{-5}$ M concentration. NTX was given as a single drop (0.05 ml) to the central cornea of the right eye, with the lower eyelid held away from the eye to avoid overflow. NTX or vehicle was administered once at 0700 hours, or at 0700, 1100, 1400, and 1700 hours for 1 or 5 days, beginning on the 9th week after induction of diabetes.

Topical Administration of Insulin

Bovine insulin (Sigma-Aldrich) was prepared in Vigamox (Alcon), and utilized at a concentration of 1 U, with a single drop administered to the central cornea of the eye according to Zagon et al. (*Arch Opthalmol.* 2007; 125: 1082-1088). Insulin or vehicle was applied topically at 0800 hours.

Data Analysis

For body weights and glucose measurements, Student two-tailed t-tests were utilized. With Schirmer tests and aesthesiometer measurements, one-way analysis of variance with Newman-Keuls post tests was employed because measurements were conducted on a random sample of two-thirds of the rats in each group.

Results
Induction of Diabetes

All rats weighed 245±6 g at the time of STZ injections (FIG. 1A). Normal rats gained approximately 216 g over the course of 8 weeks. Rats in the DB group were comparable in body weight to Normal animals until 2 weeks after injection of STZ. At this time, the DB group had a 10% reduction ($p<0.001$) in body weight relative to Normal animals. DB rats weighed significantly less (approximately 17-29%) than Normal rats beginning on week 2 and continuing throughout the course of the 8-week study.

Figure 1B:
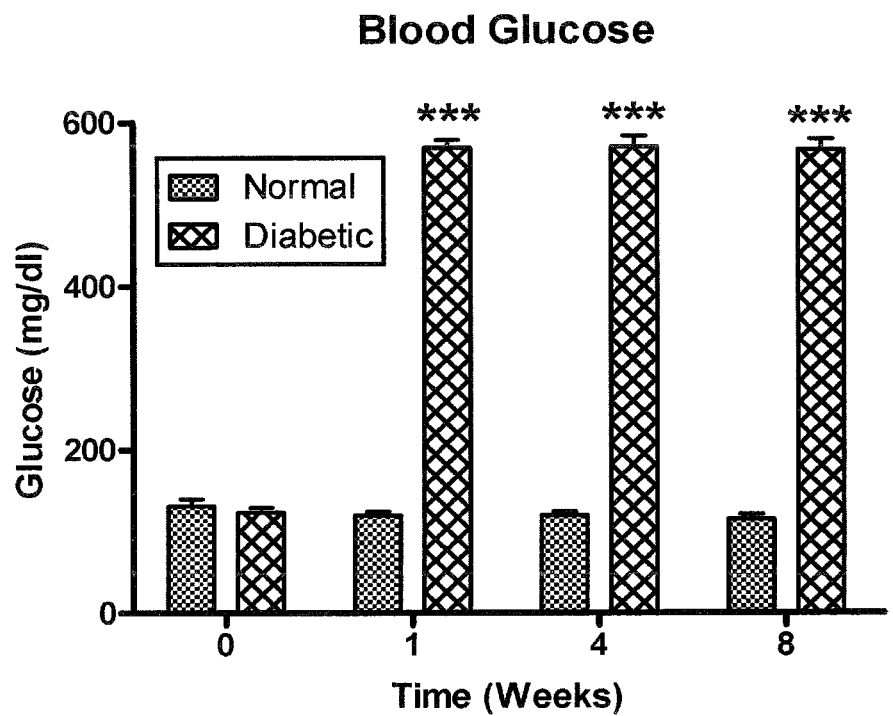

Baseline glucose readings were 131±8 mg/dL for all rats (FIG. 1B), and these values were maintained throughout the study in the Normal group. Rats receiving STZ became hyperglycemic within 5 days (FIG. 1B), and had glucose levels greater than 520 mg/dl throughout the duration of experimentation.

Temporal Course of Tear Production and Corneal Sensitivity

Figure 2A:
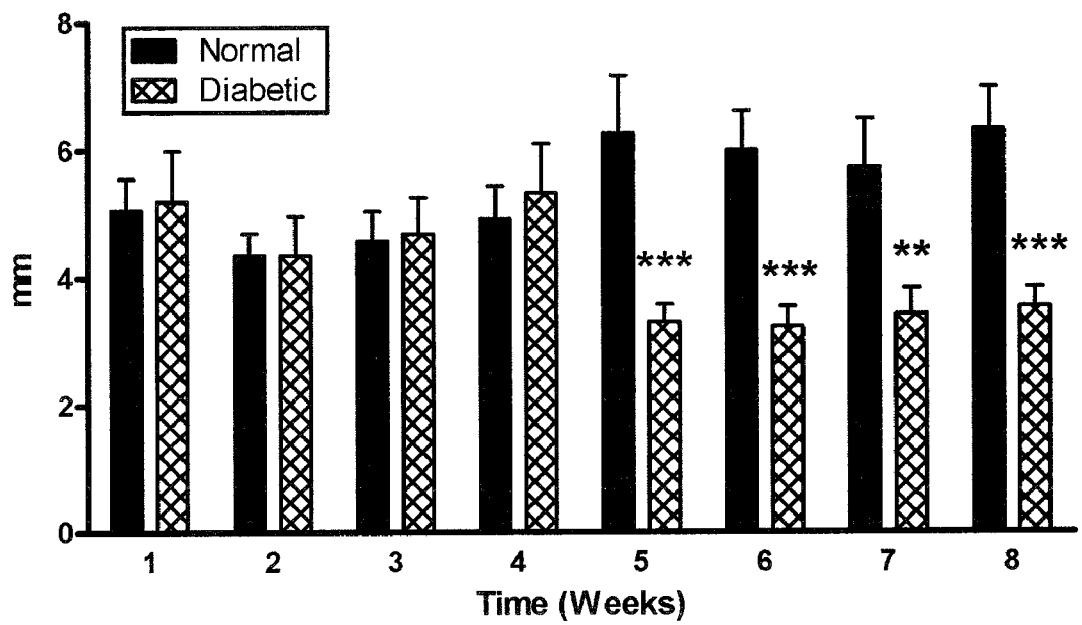
FIGS. 2A-2B. Schirmer's test (2A) and corneal sensitivity (2B) measured at weekly intervals after induction with STZ. Data are expressed as means±SEM for 15 Normal and 25 Diabetic animals at each time point. Significantly different from Normal rats at $p<0.05$ (*), $p<0.01$ (), or $p<0.001$ (*).
Figure 2B:
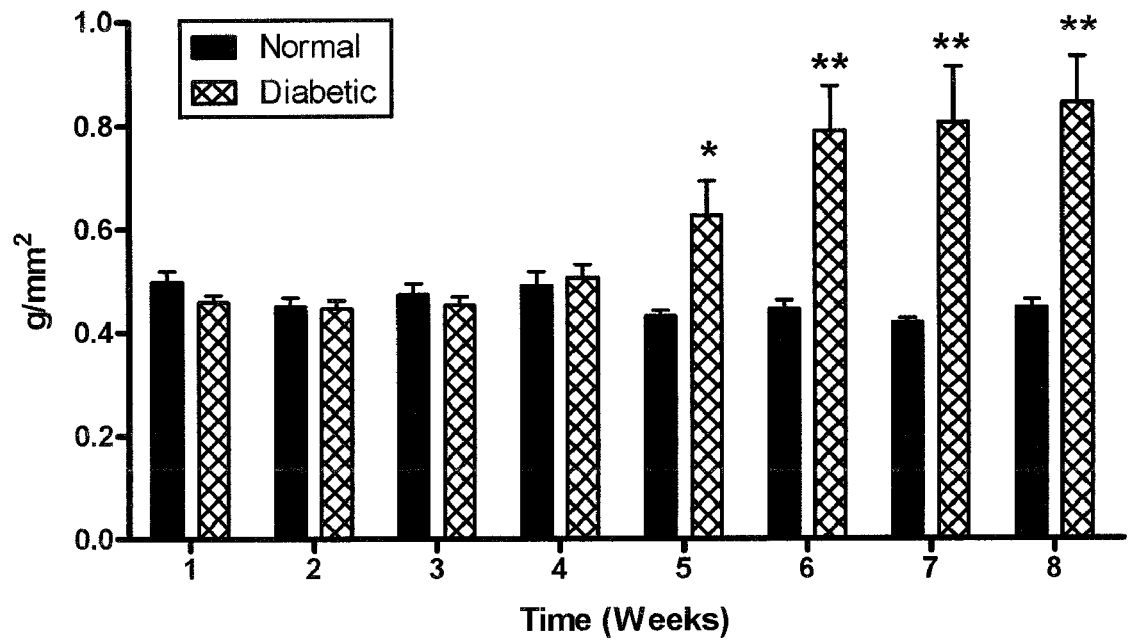

Tear production as measured by the Schirmer test (FIG. 2A), and corneal sensitivity as determined with an aesthesiometer (FIG. 2B), in DB rats were comparable to Normal animals for the first 4 weeks after injections with STZ. Beginning on week 5, and continuing thereafter, the DB rats had decreases of 40-47% in the Schirmer score and a 1.5-1.9-fold reduction in corneal sensitivity.

Tear Production and Topical Naltrexone Treatment

Figure 3A:
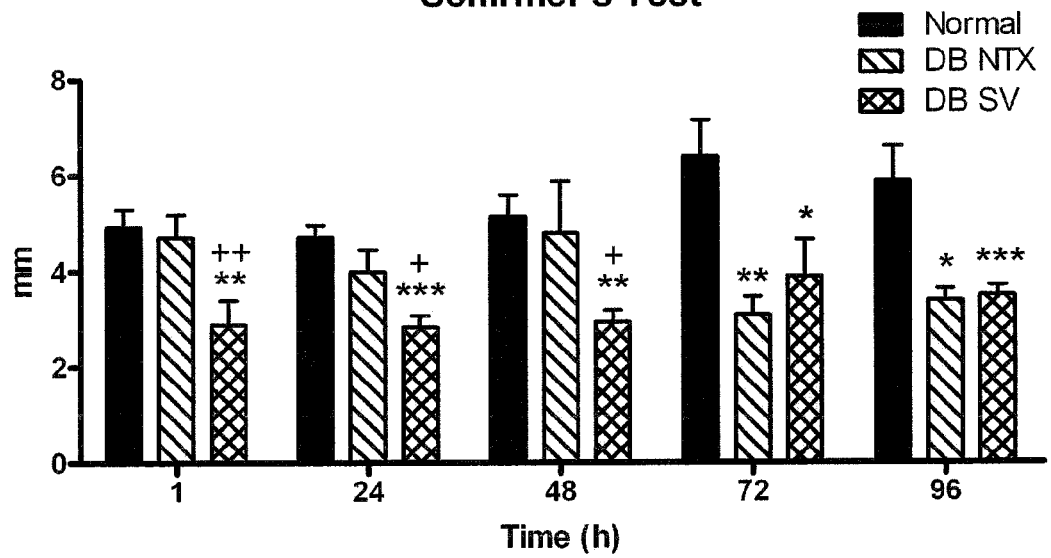
FIGS. 3A-3B. Schirmer's test (3A) and corneal sensitivity (3B) of rats given 1 drop of topical NTX (DB NTX) or vehicle (DB SV), as well as untreated animals subjected to vehicle (Normal), to the cornea. Data are expressed as means±SEM for 5-10 rats/group at each time point. Significantly different from Normal rats at $p<0.05$ (*), $p<0.01$ (), or $p<0.001$ (*), and DB rats receiving NTX at $p<0.05$ (+), $p<0.01$ (++), or $p<0.001$ (+++).

Topical administration of 1 drop of NTX restored tear secretion to the DB rat within 1 hour (FIG. 3A). Normal and DB NTX rats had comparable Schirmer scores, whereas the DB SV rats exhibited basal tear production that was reduced by over 39% from each group. Tear production for the DB rats subjected to 1 drop of NTX was similar to Normal animals for at least 48 hours after administration. However, the DB SV rats were reduced by 29-43% from the Normal and DB NTX rats at both 24 and 48 hours.

Figure 4A:
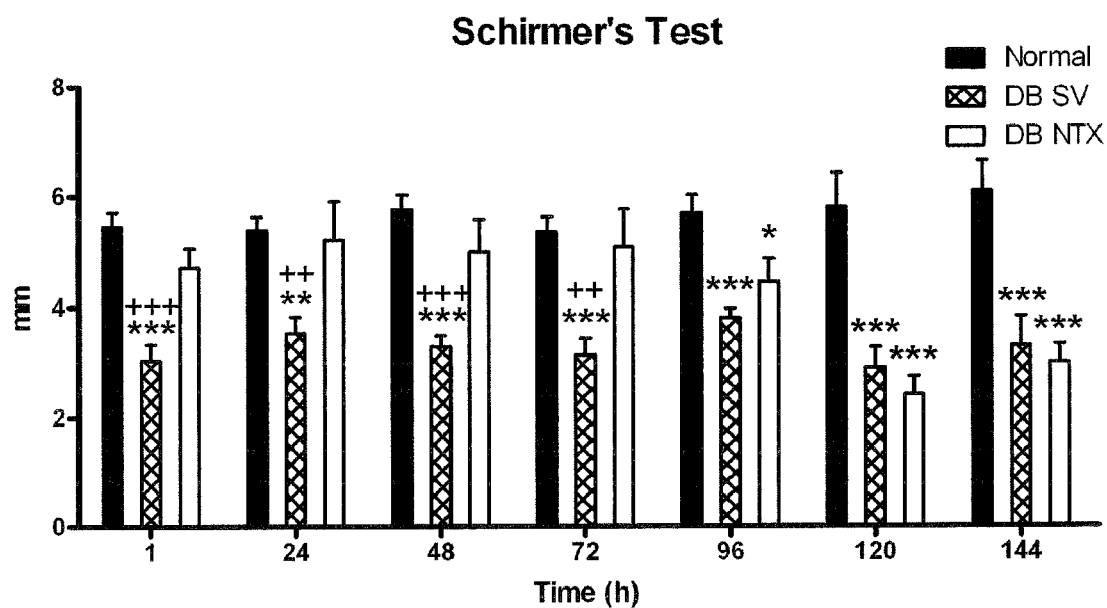
FIGS. 4A-4B. Schirmer's test (4A) and corneal sensitivity (4B) of rats given topical NTX (DB NIX) or vehicle (DB SV), as well as untreated animals subjected to vehicle (Normal), for 1 day (q.i.d.) to the cornea. Data are expressed as means±SEM for 6-11 animals/group at each time point. Significantly different from Normal rats at $p<0.05$ (*), $p<0.01$ (), or $p<0.001$ (*), and DB rats receiving NTX at $p<0.05$ (+), $p<0.01$ (++), or $p<0.001$ (+++).
Figure 4B:
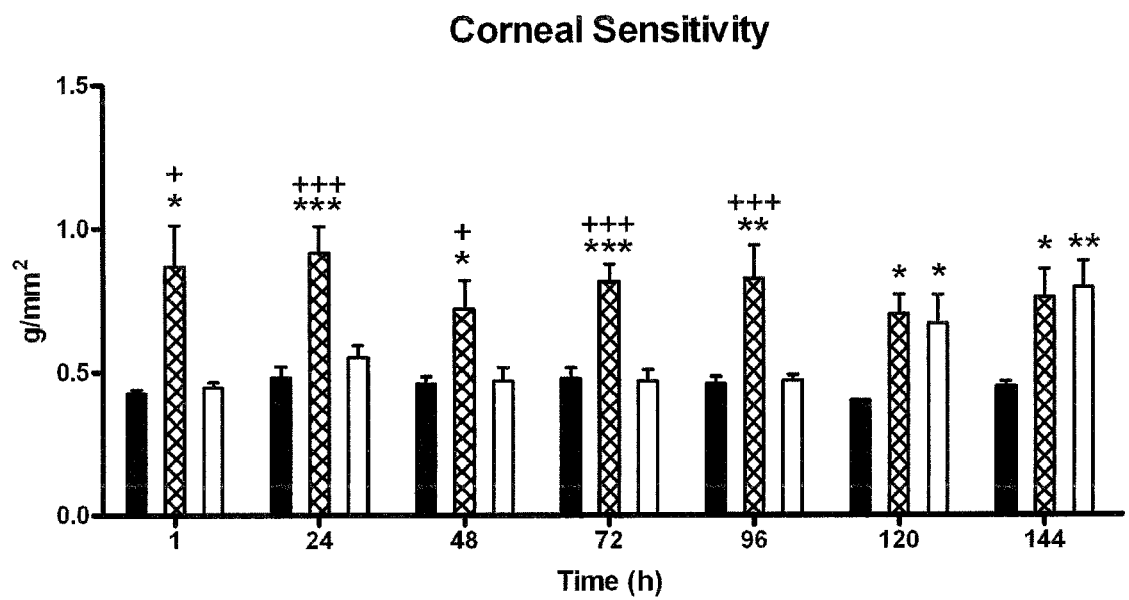
Figure 5A:
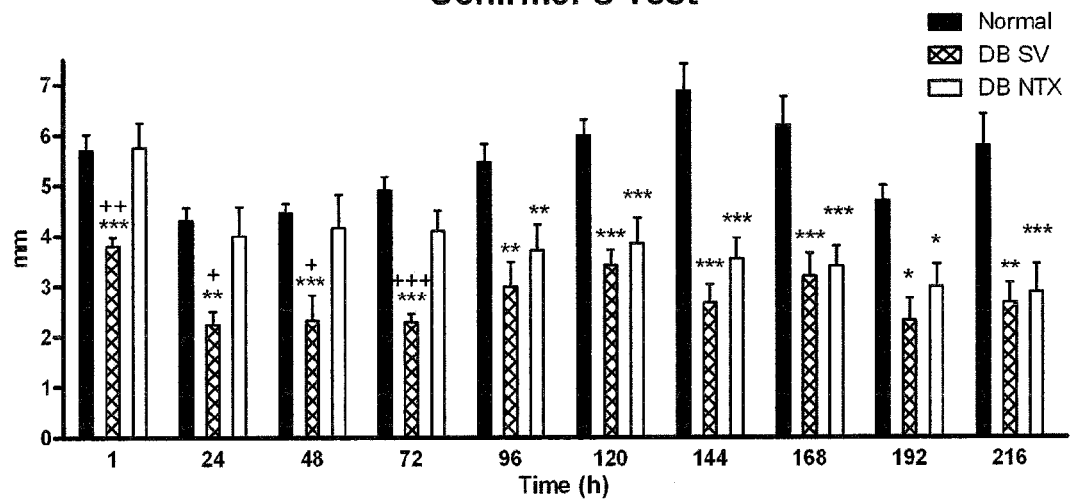
FIGS. 5A-5B. Schirmer's test (5A) and corneal sensitivity (5B) of rats given topical NTX (DB NTX) or vehicle (DB SV), as well as untreated animals subjected to vehicle (Normal), for 5 days (q.i.d.) to the cornea. Data are expressed as means±SEM for 5-10 rats/group at each time point. Significantly different from Normal rats at $p<0.05$ (*), $p<0.01$ (), or $p<0.001$ (*), and DB rats receiving NTX at $p<0.05$ (+), $p<0.01$ (++), or $p<0.001$ (+++).

DB rats receiving topical treatment with NTX for 1 (FIG. 4) or 5 (FIG. 5) days q.i.d. had Schirmer scores that were comparable to Normal rats beginning 1 hour after termination of drug exposure and extending for at least 3 days thereafter (FIGS. 4, 5). However, the DB animals receiving sterile vehicle (i.e., DB SV group) had tear production scores that were reduced from both the Normal and the DB NTX groups by 32-53%. By 96 hours after termination of either 1 or 5 days of NTX administration (q.i.d.), the effects of NTX had attenuated so that tear production in the DB NTX group was reduced by 22-59% from Normal animals, and had similar levels of tears to the DB SV group. Measurements of the Schirmer test for the DB NTX group remained significantly reduced from the Normal animals for at least 3 to 6 days after completing NTX treatment.

Corneal Sensitivity and Topical Naltrexone Treatment

Figure 3B:
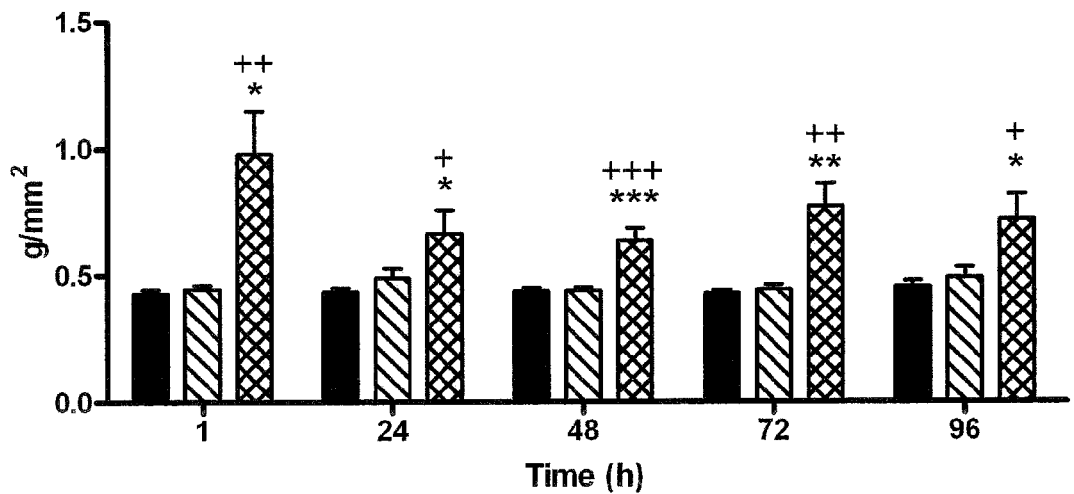

Topical administration of 1 drop of NTX restored corneal sensitivity to DB rats within 1 h (FIG. 3B) and extended for the entire 96 hour period of the experiment, with Normal and DB NTX rats having comparable measurements; the DB SV rats had a 2.3-fold decrease in sensitivity from the Normal and DB NTX groups. However, the DB SV rats had a reduction in corneal sensitivity of 1.4- to 1.8-fold from the Normal and DB NTX rats over the entire 96 hour course of the study.

Figure 5B:
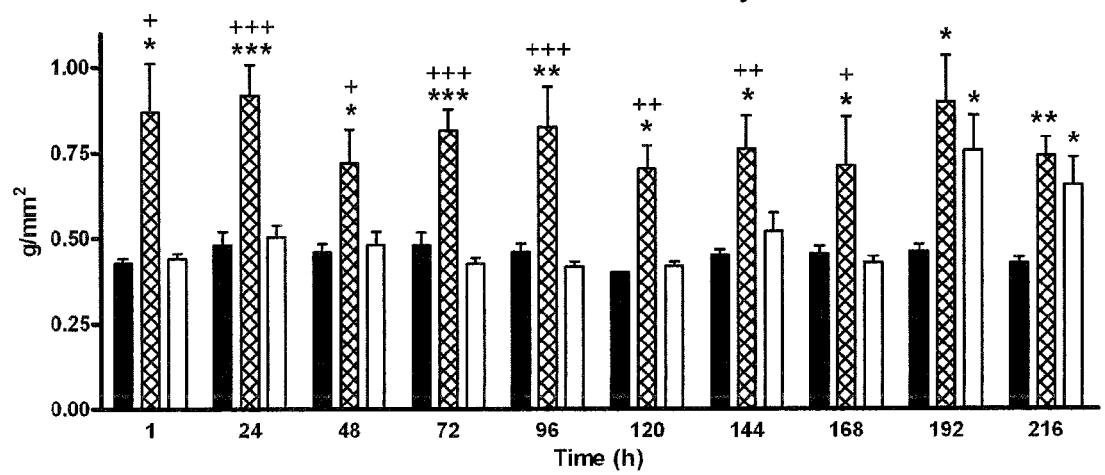

In contrast, DB rats receiving topical treatment with NTX for 1 or 5 days q.i.d. had corneal sensitivity scores that were comparable to Normal rats beginning 1 h after termination of drug exposure and extending for at least 4 days thereafter (FIGS. 4B, 5B). However, the DB animals receiving sterile vehicle (i.e., DB SV group) had sensitivity scores that were reduced from both the Normal and the DB NTX groups by 1.5- to 2.0-fold. At 120 hours after termination of the 1 day of treatment with NTX (q.i.d.), the NTX effect had expired so that the DB NTX group of rats was reduced by 1.8-fold in sensitivity from the Normal animals, and had similar levels of sensitivity to the DB SV group. At 192 hours after termination of the 5 day treatment with NTX (q.i.d.), the DB NTX group was reduced 1.9-fold in sensitivity from the Normal animals, and had comparable values to the DB SV group. At 216 hours after termination of the 5 day regimen of NTX, the DB NTX remained 1.7-fold reduced in corneal sensitivity from the Normal animals.

Non-Invasive Measurements of Corneal Integrity

Examination with a hand-held slit lamp during and after NTX administration did not reveal any abnormalities of the ocular surface in any animal.

Tear Production and Corneal Sensitivity: Topical Insulin Treatment

Figure 6A:
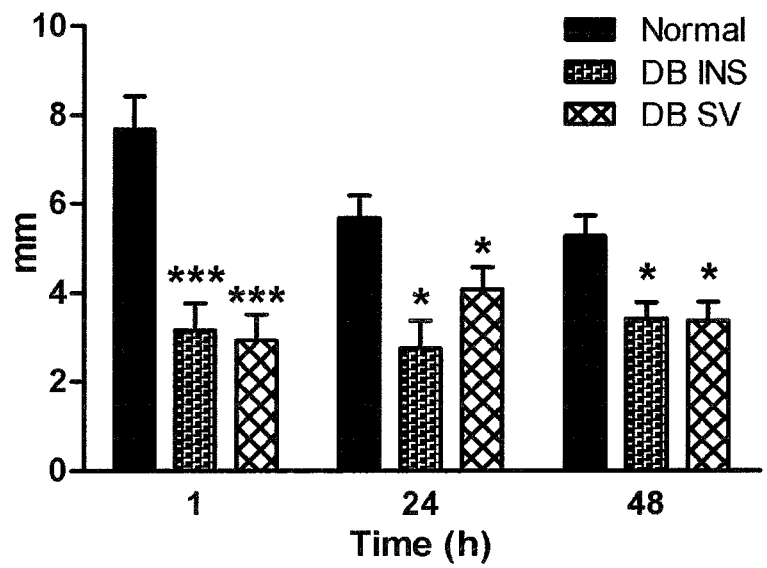
FIGS. 6A-6B. Schirmer's test (6A) and corneal sensitivity (6B) of rats given 1 drop of topical insulin NTX (DB INS) or vehicle (DB SV), as well as untreated animals subjected to vehicle (Normal), to the cornea. Data are expressed as means±SEM for 5-10 rats/group at each time point. Significantly different from Normal rats at p<0.05 (*), p<0.01 (), or p<0.001 (*), and DB rats receiving insulin at p<0.05 (+).

Topical administration of 1 drop of INS had no effect on tear production in DB rats (FIG. 6A). The Schirmer score for the DB INS group was decreased from Normal rats by 35-58% at the 1, 24, and 48 hour time points, whereas the DB SV group was subnormal by 27-61%. Thus, the values for the DB INS and DB SV groups were comparable.

Figure 6B:
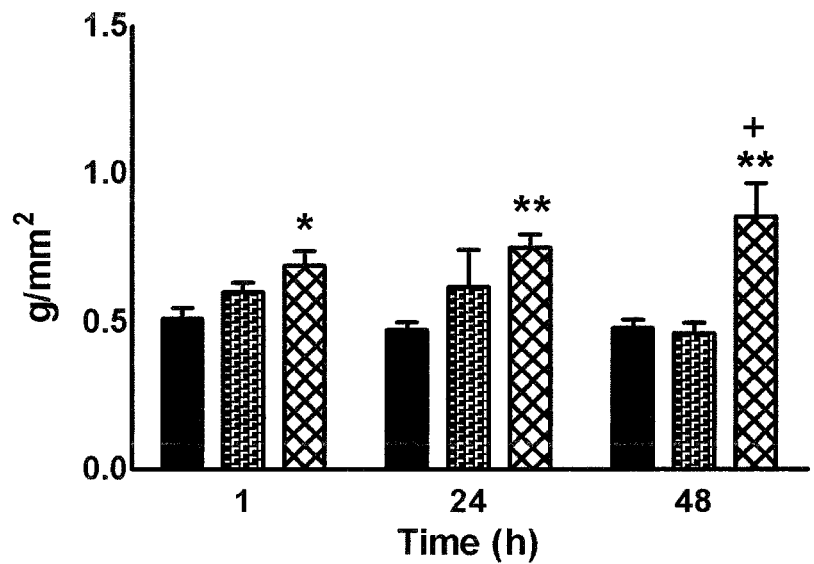

Corneal sensitivity of the DB rats receiving topical INS did not differ from the Normal animals at any time point (FIG. 6B). However, the rats treated with vehicle had reductions in aesthesiometer scores ranging from 1.3- to 1.8-fold from Normal subjects, and 1.1- to 1.9-fold from the DB INS group. Corneal sensitivity for Normal and DB INS rats were comparable at 1, 24, and 48 h time points.

Although the rat model of dry eye in this example was diabetic, naltrexone is believed to treat dry eye regardless of the cause of dry eye, e.g., regardless whether dry eye was caused by corneal injury in a diabetic individual or other causes in a non-diabetic individual.

Example 2

Rabbit Models of Dry Eye

Several rabbit models of dry eye have been established, including a lacrimal gland ablation model (*Invest. Opthalmol.* *Vis Sci* 1988; 29: 374-8), a lacrimal gland denervation model (*Current Eye Res* 1999; 18: 455-66), and an inflammation-induced dry eye model (*J. Ocul Pharmacol Ther* 2005; 21: 139-48). The teachings of these references are incorporated in their entirety.

Naltrexone and naloxone are tested in these (non-diabetes) rabbits after dry eye is induced.

Example 3

Mouse Models of Dry Eye

Experimental mouse models of dry eye have also been established, as reported in *Eye Contact Lens* 2005; 31: 175-8 and *Invest Opthalmol Vis Sci* 2003; 44:4223-9. The teachings of these references are incorporated in their entirety.

Naltrexone and naloxone are tested in these (non-diabetes) mice after dry eye is induced.

Example 4

Figure 7:
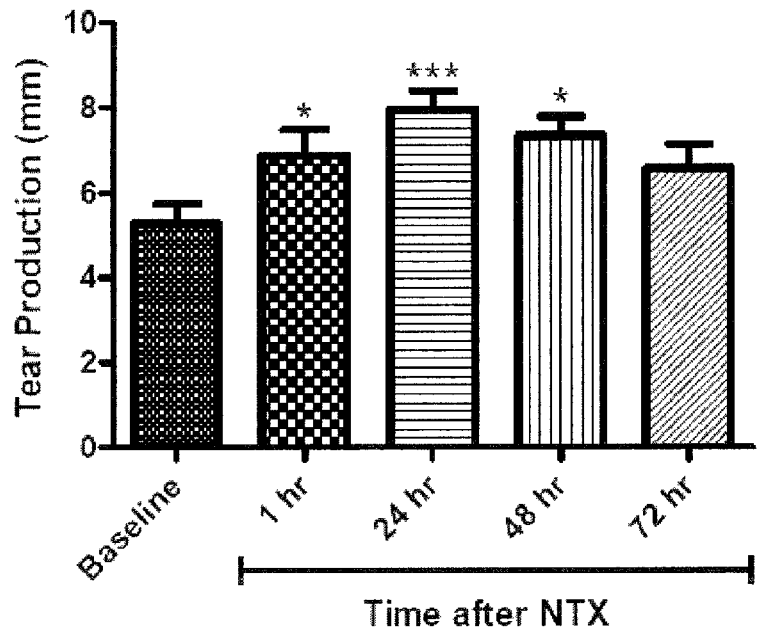
FIG. 7. Tear production of Normal rats with Dry Eye (upper panel) and "Wet" eye (lower panel). Animals were measured at baseline, and given 1 drop of topical $10^{-6}$ M naltrexone hydrochloride (NTX). The horizontal black line represents mean baseline for comparisons. Data are expressed as mean (SEM) for 7 rats per group at each time point except 48 hr wherein n=3 rats. Significantly different from baseline values at p<0.05 (*) or p<0.001 (***).
Figure 7:
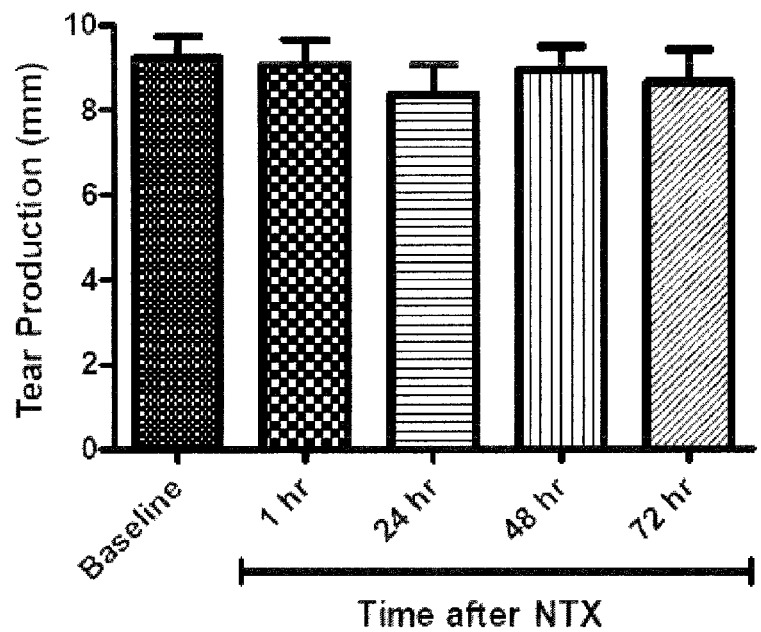

Sprague-Dawley rats, males of 15-22 weeks of age, were tested for dry eye and therapeutic effects of opioid antagonists. As shown in FIG. 7, the upper panel shows that dry eye does occur in normal rats (compare the baseline to the bottom baseline for a "wet" eye). When one drop of NTX was given in a VIGAMOX solution (Alcon Inc., Hünenberg, Switzerland) at $10^{-6}$M, dry eye was reversed within an hour. The "wet" eye was maintained at 24 and 48 hr, and was back to dry eye by 72 hr. Further, in the bottom panel, animals with "wet" eye had no change in moisture with the addition of one drop of NTX. All of these measures used a test called the Schirmer Test, as described in Example 1 (the same test used for humans).

What is claimed is:

1. A method of treating dry eye in a subject in need of such treatment, comprising topical administration to the eye or eyes of said subject a composition comprising an effective amount of naltrexone, naloxone or a pharmaceutically acceptable salt thereof and a pharmaceutically acceptable carrier.

2. The method of claim 1, wherein said composition is formulated as a solution and is administered drop wise to the eye or eyes of said subject.

3. The method of claim 1, wherein naltrexone, naloxone or said pharmaceutically acceptable salt thereof is present in said composition at a concentration of at least $10^{-7}$ M.

4. The method of claim 1, wherein said composition is administered at least once daily or every other day to said subject.

5. A composition for treating dry eye comprising an effective amount of naltrexone, naloxone or a pharmaceutically acceptable salt thereof and a pharmaceutically acceptable carrier.

6. The composition of claim 5, wherein said composition is formulated as a solution.

7. The composition of claim 5, wherein naltrexone, naloxone or said pharmaceutically acceptable salt thereof is present in said composition at a concentration of at least $10^{-7}$ M.

8. The composition of claim 5, further comprising at least one additional active ingredient for treating dry eye.

* * * * *